United States Patent [19]

Saito et al.

[11] Patent Number: 4,787,997
[45] Date of Patent: Nov. 29, 1988

[54] ETCHING SOLUTION FOR EVALUATING CRYSTAL FAULTS

[75] Inventors: Yoshihiko Saito, Yokosuka; Yoshiaki Matsushita, Kawasaki, both of Japan

[73] Assignee: Kabushiki Kaisha Toshiba, Kawasaki, Japan

[21] Appl. No.: 163,033

[22] Filed: Mar. 2, 1988

[30] Foreign Application Priority Data

Mar. 4, 1987 [JP] Japan .................................. 62-49042

[51] Int. Cl.$^4$ ........................ H01L 21/306; B44C 1/22
[52] U.S. Cl. .................................. 252/79.4; 156/657; 156/662; 252/79.3
[58] Field of Search ..................... 252/79.2, 79.3, 79.4; 156/647, 657, 659.1, 662

[56] References Cited

U.S. PATENT DOCUMENTS 3,272,748  9/1966  Szkudlapski ........................ 252/79.3
4,681,657  7/1987  Hwang et al. .................. 252/79.4 X

OTHER PUBLICATIONS

W. C. Dash, "Copper Precipitation on Dislocations in Silicon", Journal of Applied Physics, vol. 27, No. 10, pp. 1193–1195, Oct. 1956.

Jenkins, "A New Preferential Etch for Defects in Silicon Crystals", J. Electrochem. Soc., vol. 124, No. 5, pp. 757–762, May 1977.

d'Aragoa, "Dislocation Etch for (100) Planes in Silicon", J. Electrochem. Soc., vol. 119, No. 7, pp. 948–951, Jul. 1972.

Primary Examiner—William A. Powell
Attorney, Agent, or Firm—Finnegan, Henderson, Farabow, Garrett, & Dunner

[57] ABSTRACT

An etching solution used for evaluating crystal defects in a silicon wafer is disclosed. The etching solution is characterized by consisting of acetic acid, hydrofluoric acid, nitric acid, silver nitrate, and copper nitrate, and is very advantageous in consideration of the operator's health, since it does not contain $Cr^{6+}$. The etching solution has a sufficiently high etching rate and detection properties.

2 Claims, 5 Drawing Sheets

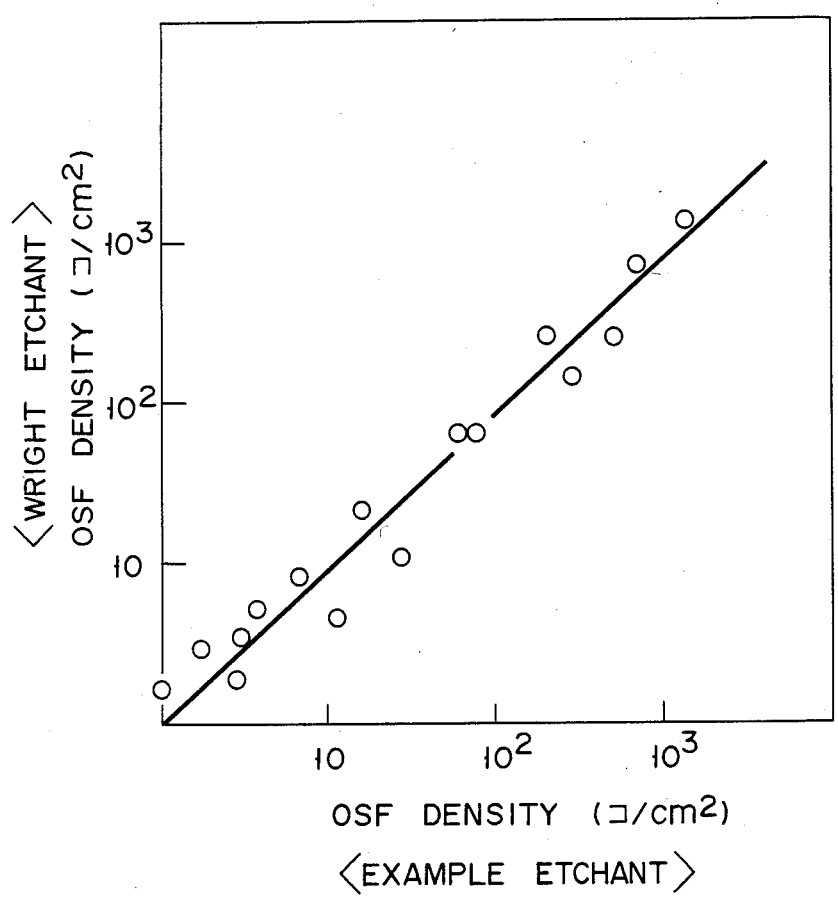
F I G. 2

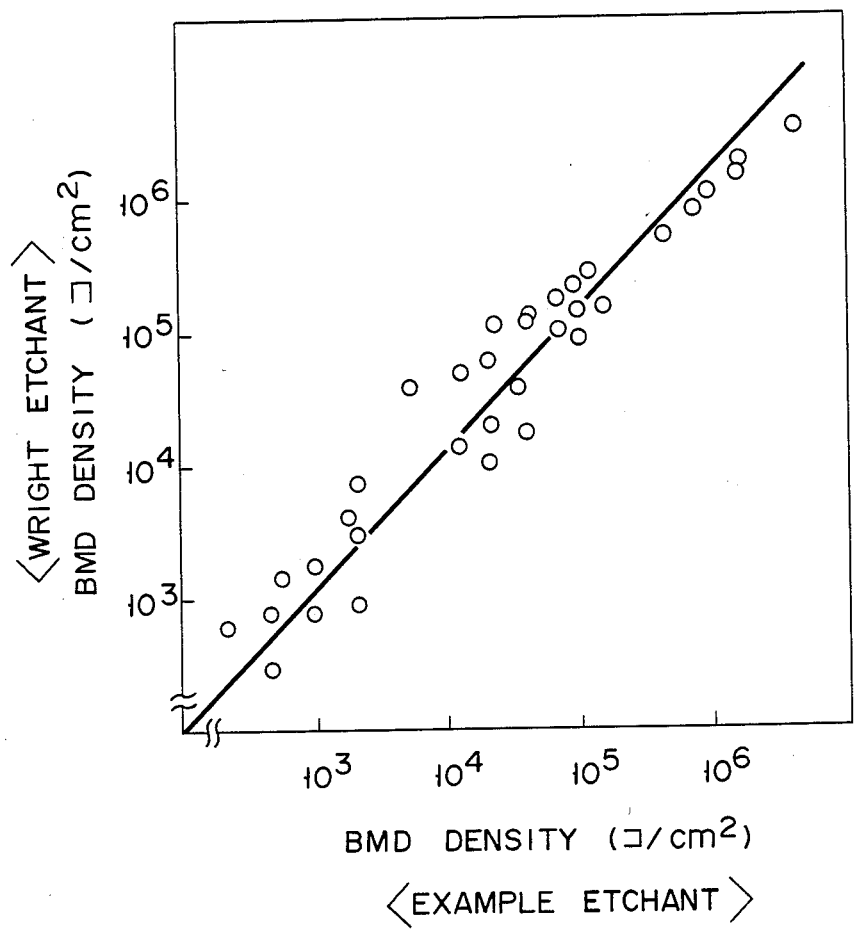
F I G. 3

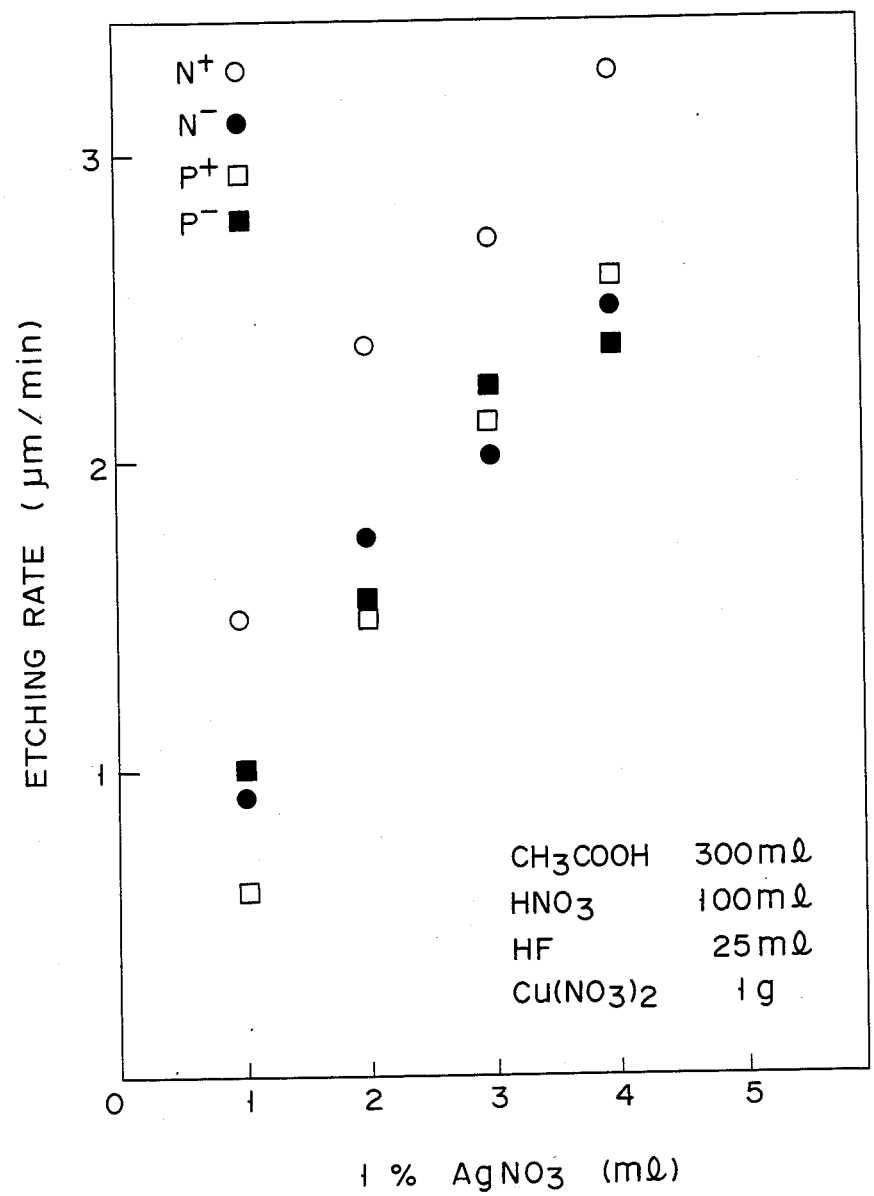
F I G. 4

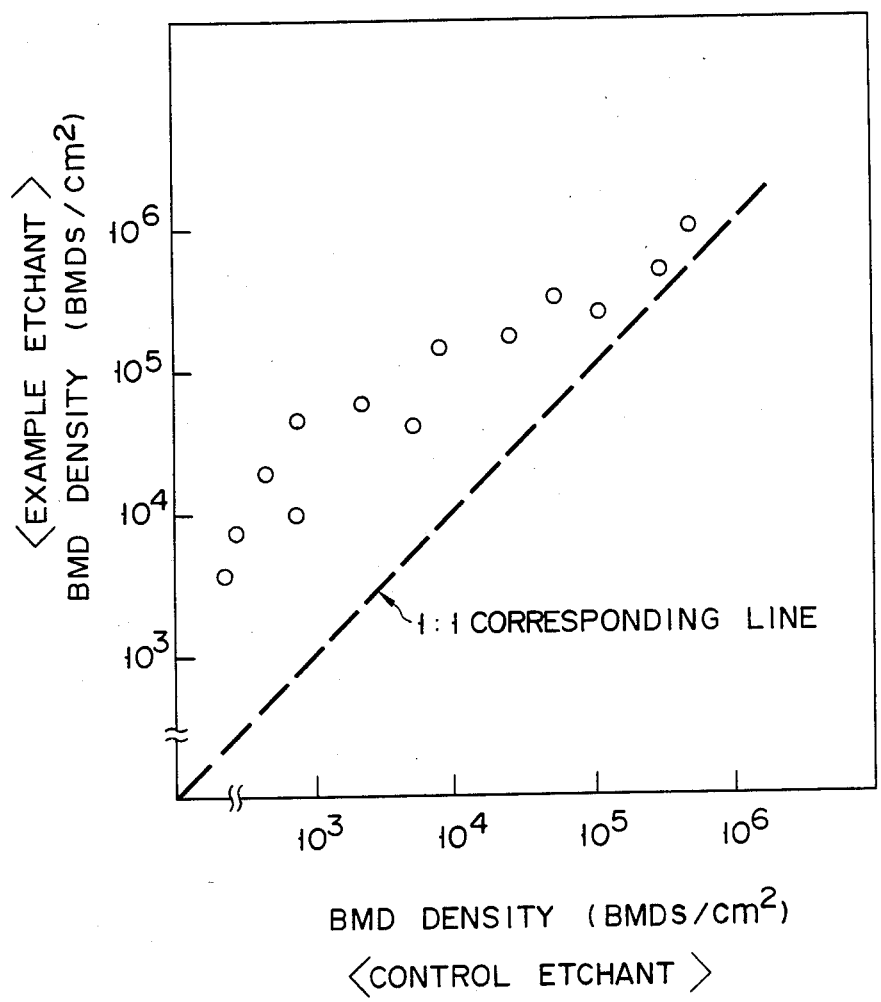
F I G. 5

ETCHING SOLUTION FOR EVALUATING CRYSTAL FAULTS

BACKGROUND OF THE INVENTION

1. Field of the Invention

The present invention relates to an etching solution for evaluating crystal defects and, more particularly, to an etching solution used to evaluate a density of Oxidation Induced Stacking faults (to be referred to as OSFs hereinafter) and/or Bulk Microdefects (to be referred to as BMDs hereinafter) present in a silicon wafer.

2. Description of the Related Art

Crystal faults present in a silicon wafer largely affect the characteristics of an element such as a transistor and the like formed on the wafer. In order to obtain good characteristics, crystal defects present in an element region must be eliminated as much as possible. Therefore, in a process technique of manufacturing a semiconductor device, many studies for suppressing generation of crystal defects have been made.

In order to promote such studies, a crystal defects density in a silicon wafer must be precisely, easily, and quickly evaluated. For this purpose, the following method is used. More specifically, a wafer surface is etched using an etching solution having a selectivity with respect to crystal defects such as OSFs and BMDs, and optically detectable pits are formed on a defects portion of the wafer surface. The pits are counted, and the count result is converted to a value per unit volume, thereby evaluating a defects density.

Conventional etching solutions used in the above evaluation method will be described. These etching solutions contain an oxidizing agent for oxidizing silicon and hydrofluoric acid for dissolving silicon dioxide produced upon oxidation of silicon.

Dash etchant

A Dash etchant is an etching solution having a composition ratio of hydrofluoric acid: nitric acid: acetic acid = 1:3:12.

The etching character of the Dash etchant does not depend on crystal orientation, and can be advantageously applied to any crystal orientation. However, this solution requires 30 minutes or more for etching. As an etching solution free from the drawback of the Dash etchant, the following etching solution is known.

Sirtl etchant

A Sirtl etchant is an etching solution having a composition ratio of $H_2O$: hydrofluoric acid: $CrO_3$ = 1:0.4:0.2. This etching solution can provide a relatively high etching rate of about 1 $\mu m/min$. However, this solution has a dependency with respect to crystal orientation. The etching solution can be applied to crystal orientation having indices of face of (111) and (110). However, if the etching solution is applied to crystal orientation having an index of face of (100), pits corresponding to crystal defects cannot be easily formed.

Secco etchant

A Secco etchant is an etching solution consisting of 100 cc of hydrofluoric acid, and 50 cc of a 0.15 mol% aqueous $K_2Cr_2O_7$ solution. This etching solution can provide a relatively high etching rate of about 1.2 $\mu m/min$. However, since bubbles are easily attached to a silicon wafer to be etched during etching, ultrasonic cleaning must be performed.

Wright etchant

A Wright etchant is an etching solution consisting of 69 cc of hydrofluoric acid, 30 cc of nitric acid, 30 cc of a 5 mol% aqueous $CrO_3$ solution, 2 g of copper nitrate, 60 cc of acetic acid, and 60 cc of water. This etching solution can provide a relatively high etching rate of about 1 $\mu m/min$. This solution can be applied to any crystal orientation, and the resultant pits have sharp edges and are easy to observe. For this reason, this etching solution is most popular.

As described above, the Sirtl, Secco, and Wright ecthant have satisfactory etching rates but contain hexavalent chrom ($Cr^{6+}$) toxic to a human body. For this reason, problems in respects of operator's health and environmental preservation are posed.

SUMMARY OF THE INVENTION

It is an object of the present invention to provide an etching solution for evaluating crystal defects of a silicon wafer, which can complete desired etching in a short period of time, and does not contain $Cr^{6+}$.

In order to achieve the above object, there is provided an etching solution consisting of: acetic acid, hydrofluoric acid, nitric acid, silver nitrate, and copper nitrate.

BRIEF DESCRIPTION OF THE DRAWINGS

FIG. 2 is a graph showing the relationship between OSF density evlluation using an etching solution of the present invention and OSF density evaluation using the Wright etchant;

FIG. 3 is a graph showing the relationship between BMD density evaluation using an etching solution of the present invention and BMD density evaluation using the Wright etchant;

FIG. 4 is a graph showing the relationship between an amount of copper nitrate to be added and an etching rate by an etching solution of the present invention; and FIG. 5 is a graph demonstrating that the etching solution of the present invention has higher selectivity with respect to BMDs than the etching solution excluding copper nitrate.

DETAILED DESCRIPTION OF THE PREFERRED EMBODIMENT

Figure 1:
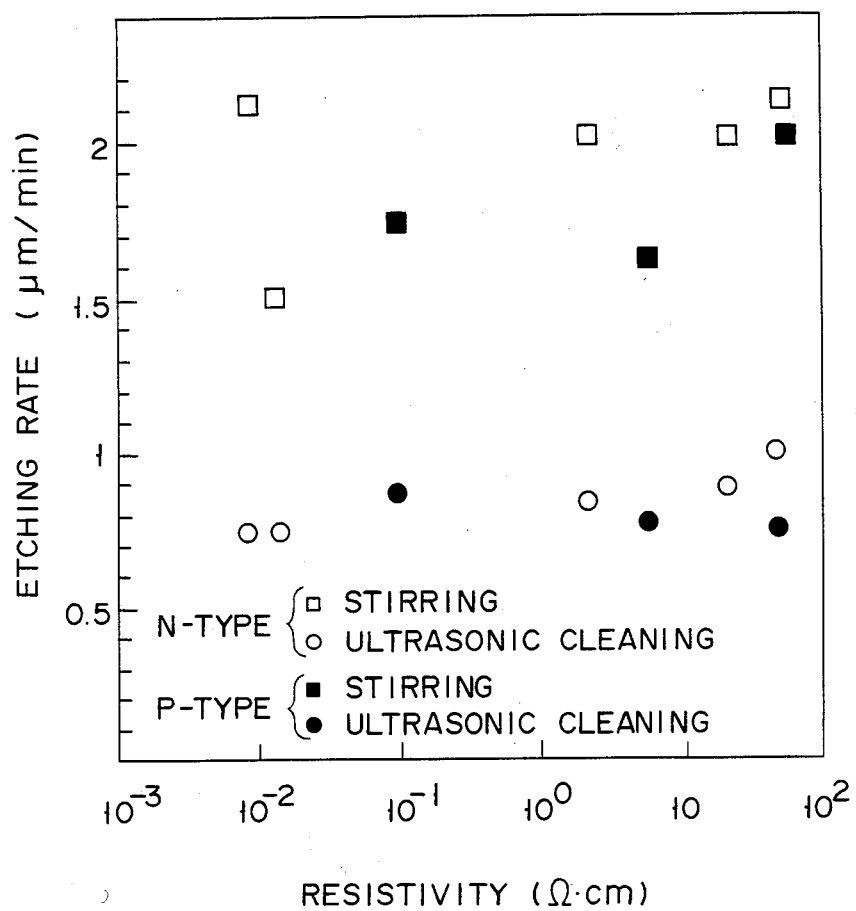
FIG. 1 is a graph showing the relationship between an etching rate by an etching solution of the present invention and a resistivity of a silicon wafer to be etched.

If an etching solution of the present invention contains too much acetic acid, the concentration of an oxidizing agent is decreased accordingly. Therefore, an oxidization effect is impaired, and a sufficiently high etching rate cannot be obtained. On the other hand, if an amount of acetic acid is too small, an etching rate becomes too fast, and surface roughness can easily occur. As a result, it is not easy to observe OSFs or BMDs.

Hydrogen fluoride has an effect of dissolving $SiO_2$ formed by an oxidizing agent upon the oxidation of silicon. Therefore, if an amount of hydrogen fluoride is too small, a sufficiently high etching rate cannot be obtained. On the other hand, if the amount of hydrogen fluoride is too large, an etching rate becomes too fast, and surface roughness can easily occur.

Nitric acid serves as an oxidizing agent of silicon. If an amount of nitric acid is too large, an etching rate becomes late, and surface roughness occurs.

Silver nitrate has an effect of accelerating an etching rate. Therefore, if an amount of silver nitrate is too small, an etching rate is decreased, and efficiency is thereby degraded. On the other hand, if the amount of silver nitrate is too large, an etching rate becomes too fast, and hence, it is difficult to control an amount of etching.

Copper nitrate has an effect of increasing the selectivity of an etching solution according to the present invention with respect to BMDs. Therefore, an appropriate amount of copper nitrate to be added is determined by the type of crystal defects to be detected and in consideration of their proportion to the other components in the solution.

Based on the above findings, a preferable composition of an etching solution according to the present invention is as follows:

Acetic acid: 250 to 300 ml
Hydrofluoric acid: 20 to 300 ml
Nitric acid: 60 to 120 ml
Aqueous silver nitrate solution: 1 to 5 ml
Copper nitrate: 0.1 to 0.2 g The present invention will be described in more detail by way of its examples.

EXAMPLE 1

A crystal defects evaluation etching solution having the following composition was prepared:

Acetic acid: 300 ml
49% hydrofluoric acid: 25 ml
70% nitric acid (available from Hikita Kagaku Kogyo KK): 100 ml
1% aqueous silver nitrate solution: 5 ml
Copper nitrate: 1 g A silicon wafer surface having a crystal orientation of <100> was oxidized by dry $O_2$ at 1,000° C. for 16 hours to generate OSFs and BMDs. The etching solution thus prepared as described above was applied to the silicon wafer with the crystal defects, and the characteristics of the etching solution were examined.

In this Example, silicon wafers having various resistivities were etched to check their dependencies on the resistivities (i.e., impurity concentration). Note that experiments were conducted for both p- and n-type silicon wafers. Etching was performed under two different conditions, i.e., while mechanically stirring the etching solution, and while stirring the etching solution using ultrasonic waves. Results are summarized in FIG. 1.

As can be seen from the results shown in FIG. 1, the etching solution of the present invention does not largely depend on the conductivity type and resistivity of the silicon wafer. In addition, a sufficiently high etching rate of 1.5 to 2.2 μm/min can be obtained. Therefore, the etching solution of the present invention can be widely applied without depending on the types of silicon wafer used.

EXAMPLE 2

In this Example, the results of the OSF evaluation using the etching solution as prepared in Example 1 and those using the conventional Wright etchant, are compared.

The silicon wafer in which OSFs were generated by following the same procedures as in Example 1, was divided into two pieces. The surface of one piece was etched by the etching solution of the present invention for 1 minute. The surface of the other piece was etched by the Wright etchant for 2 minutes. The OSFs on both the wafer pieces were counted using a differential interference microscope to obtain the OSF densities. The relationship between the OSF densities obtained with the etching solution of the present invention and the Wright etchant was examined. Results are summarized in FIG. 2.

As can be seen from the results in FIG. 2, the etching solution of the present invention has OSF detection properties equivalent to those of the Wright etchant.

EXAMPLE 3

In this Example, the results of the BMD evaluation using the etching solution prepared in Example 1 and those using the conventional Wright etchant, are compared.

A silicon wafer in which the BMDs were generated following the same procedures as in Example 1, was cleaved along crystal face (110) to prepare a ribbon-like test piece. The cleavage face of the test piece was etched by the etching solution of the present invention for 1 minute. The cleavage face of test strip prepared from the identical wafer was etched by the Wright etchant for 2 minutes. The BMDs of these etched test strips were counted by a differential interference microscope to obtain their BMD densities. The relationship between the BMD densities obtained with the etching solution of the present invention and that of the Wright etchant was examined. Results are summarized in FIG. 3.

As can be seen from the results in FIG. 3, the etching solution of the present invention also has BMD detection properties equivalent to those of the Wright etchant.

EXAMPLE 4

In this Example, the effect of the addition of silver nitrate to the etching solution of the present invention is examined. More specifically, the etching solutions were prepared following the same procedures as in Example 1, except that an adding amount of 1% aqueous silver nitrate solution was changed. The results of the etching rates obtained with these etching solutions are summarized in FIG. 4.

As can be seen from FIG. 4, the etching rate obtained with the etching solution of the present invention is a substantially improvement in proportion to the amount of silver nitrate added.

EXAMPLE 5

In this example, an example solution prepared as in Example 1 and a control solution having approximately the same composition as that of the example solution, except that it did not contain copper nitrate, were used, and the effects of the addition of copper nitrate to the etching solution of the present invention were examined.

Cleavage faces (110) of wafers were etched using the example and control solutions following the same procedures as in Example 3, and the BMD densities were evaluated. FIG. 5 shows the results obtained with the example and control solutions.

The results shown in FIG. 5 reveal that the example solution containing copper nitrate has a higher selectivity with respect to the BMDs. Note that no difference in the etching rate was found between the example and control solutions.

As described above, since an etching solution of the present invention does not contain toxic $Cr^{6+}$, the operator's health is not endangered by using the solution. In addition, a sufficiently high etching rate can be obtained, and detection properties for both the OSFs and BMDs equivalent to those of the Wright etchant which has been widely used, can be obtained.

Note that the etching solution used in each Example is merely an example, and the present invention is not limited to these compositions.

What is claimed is:

1. An etching solution for evaluating crystal defects of a silicon wafer, comprising: acetic acid, hydrofluoric acid, nitric acid, silver nitrate, and copper nitrate.

2. An etching solution according to claim 1, wherein the contents of the components fall within the following ranges:
   acetic acid: 250 to 300 ml
   hydrofluoric acid: 20 to 300 ml
   nitric acid: 60 to 120 ml
   aqueous silver nitrate solution: 1 to 5 ml
   copper nitrate: 0.1 to 0.2 g.

* * * * *